United States Patent [19]

Fisher

[11] Patent Number: 4,657,793
[45] Date of Patent: Apr. 14, 1987

[54] FIBROUS STRUCTURES

[75] Inventor: Anthony C. Fisher, Willaston, England

[73] Assignee: Ethicon, Inc., Somerville, N.J.

[21] Appl. No.: 833,307

[22] Filed: Feb. 25, 1986

Related U.S. Application Data

[63] Continuation-in-part of Ser. No. 631,046, Jul. 16, 1984, abandoned.

[51] Int. Cl.⁴ .................. B32B 27/00; D02G 3/00
[52] U.S. Cl. .................................. 428/36; 428/286; 428/288; 428/293; 428/357; 428/374; 428/397
[58] Field of Search ............... 428/36, 287, 290, 364, 428/374, 397, 292, 293, 357, 284, 286

[56] References Cited

U.S. PATENT DOCUMENTS 3,768,118  10/1973  Ruffo et al. ................... 264/511
3,924,045  12/1975  Ogasawara et al. ......... 428/397 X
4,044,404  8/1977   Martin et al. ................. 128/156 X
4,424,250  1/1984   Adams et al. ................. 428/198
4,552,707  11/1985  How ............................... 264/40.7

*Primary Examiner*—Lorraine T. Kendell
*Attorney, Agent, or Firm*—Robert L. Minier

[57] ABSTRACT

An integral fibrous structure has a plurality of continuous polymeric filaments, individual continuous filaments extending from one side of the structure to the opposite side of the structure. The portions of the continuous filaments on one side of the structure are of a first polymeric composition and the portions of the same continuous filaments on the opposite side of the structure are of a second polymeric composition different from the first polymeric composition. The structure is built up by a continuous filament forming process where fibers are attracted to a surface (11) by electrostatic potential, the composition of the fibers being varied during the production.

7 Claims, 3 Drawing Figures

FIBROUS STRUCTURES

RELATED APPLICATIONS

This is a continuation-in-part application of co-pending patent application Ser. No. 631,046 filed July 16, 1984, now abandoned.

The invention relates to fibrous structures, for example fibrous mats or fibrous tubular structures. More particularly but not exclusively, the invention relates to fibrous synthetic vascular grafts.

In the past, it has been proposed to produce fibrous structures such as mats by a process using electrostatic attraction, where a polymer such as polyurethane in solution is ejected from a fine nozzle towards a surface, between which surface and the nozzle exists an electrostatic potential. Between the nozzle and the surface, fibers of the polymer are formed and the fibers are attracted to the surface. This process has been adapted to make tubular fibrous structures usable as synthetic vascular grafts by providing the surface in the form of a rotating mandrel so that a fibrous tube is gathered around the mandrel.

The electrostatic spinning process is described in some detail in U.S. Pat. No. 4,044,404 and proposals to use the electrostatic spinning process for making synthetic vascular grafts have been made, for example, in a paper by Annis et al. in 1978 (Trans. Am. Soc. Intern. Organs). The microstructure of the fibrous material produced during electrostatic spinning is also described in the Annis et al. paper. More recently, developments have been made in matching properties of synthetic vascular grafts to in vivo conditions, as in our co-pending U.S. application Ser. No. 499,711 filed May 31, 1983 and in controlling anistropic properties of grafts in our co-pending U.S. application Ser. No. 492,864 filed May 9, 1983 now U.S. Pat. No. 4,552,707.

According to the invention there is provided an integral fibrous structure of a plurality of continuous, polymeric filaments with some of the continuous filaments extending from one side of the structure to the opposite side of the structure. Portions of some of the continuous filaments on one side of the structure being of a first polymeric composition and the portions of those same continuous filaments on the opposite side of the structure being of a second polymeric composition different from the first polymeric composition.

The term "different polymeric composition" is intended to cover a variation of the composition of the filaments where the polymer itself does not change along the filament but, for example, an additive is present in the composition of the filament at one side of the structure but not present in that same filament at the opposite side of the structure.

The continuous filaments may include a transition portion between the portions of the filaments at the sides of the structure, and the transition portions of the continuous filaments area may have a polymeric composition comprising a mixture of the first and second polymeric compositions or may have a third polymeric composition.

The polymeric composition of the filaments may vary progressively in the continuous filaments between the two sides of the structure, and the composition of the filaments in the transition portion adjacent the one side of the structure may contain a large proportion of the first polymeric composition and the filaments in the transition portion adjacent the opposite side of the structure may contain a large proportion of the second polymeric composition.

Alternatively, the composition of the filaments may change abruptly to provide distinct layers within the structure having different polymeric compositions. There may be more than two layers in the structure.

The structure may be in the form of a mat, or may be a tubular member.

When the structure is a tubular member, the portions of the continuous filaments at the inner surface of the tubular member are preferably of the first polymeric composition to provide compatibility with material with which the inner surface will come into contact, and the portions of the same continuous filaments at the outer surface of the tubular member are preferably of the second polymeric composition to provide desirable strength characteristics and other physical properties to the tubular member.

The tubular member may be cut longitudinally to provide one or more segmental elements from the tubular wall. If the internal diameter of the tubular member is large enough, for example a few centimeters, the segmental element or elements will tend towards being planar, and may be used as pledgets.

The invention further provides a method of forming an integral fibrous structure according to the invention, which method comprises the steps of directing continuous filaments of a first polymeric composition at a surface to start building up a fibrous structure of the first polymeric composition, and altering the composition of the continuous filaments during production thereof such that the portions of the filaments at the side of the structure remote from the surface is of the second polymeric composition.

The composition of the filaments may be changed abruptly or may be varied gradually across the structure.

By way of example, one embodiment of a fibrous structure and its method of production according to the invention will now be described with reference to the accompanying drawings, in which.

Figure 1:
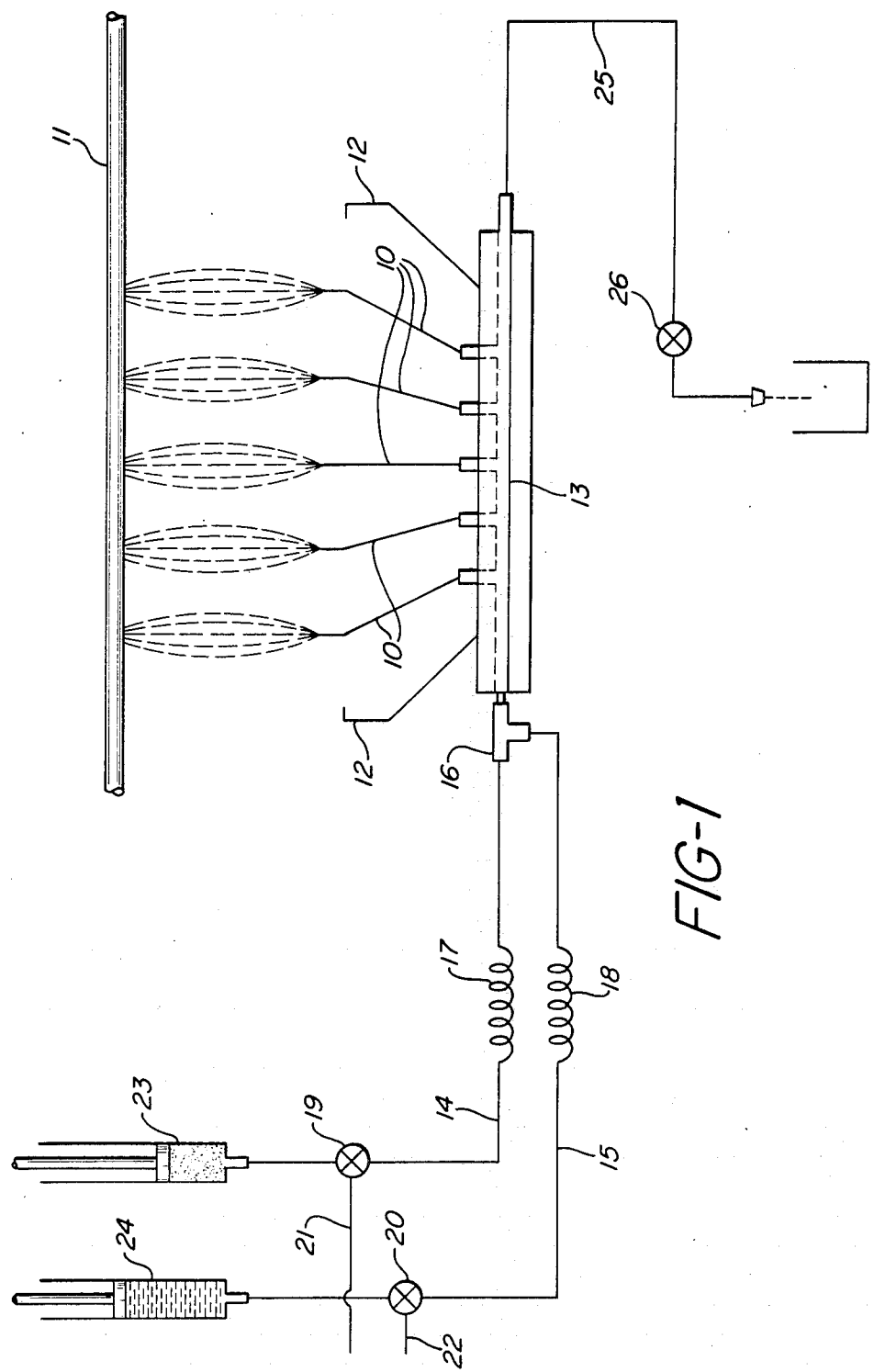
FIG. 1 is a diagrammatic view of apparatus for producing a tubular fibrous structure.

FIG. 1 shows diagrammatically apparatus for electrostatically spinning a synthetic vascular graft. Polymer solution is ejected or extruded from capillary needles 10 towards an electrostatically charged mandrel 11 rotating at several thousand resolutions per minute, for example 5000 r.p.m. Typically, the mandrel 11 is at a potential of −12 kV with respect to the needles 10. As polymer solution leaves the needles 10, continuous polymer filaments form and these filaments are attracted to the rotating electrostatically charged mandrel 11 to form a fibrous structure around the mandrel. When the fibrous structure has been built up, the structure is removed from the mandrel to provide a fibrous tube comprising randomly laid continuous filaments.

Mechanical properties of the tubular fibrous structure formed on the mandrel 11 can be controlled by variation of the speed of rotation of the mandrel, the type of polymer used and by altering the potential of auxiliary electrodes 12.

The capillary needles 10 are supplied with polymer solution from a manifold 13, the manifold 13 being supplied by tubes 14 and 15 meeting in a T connector 16. Both tubes 14 and 15 include a flexible coil 17 and 18 respectively. The tubular 14 has a valve 19 and the tube 15 has a valve 20 to enable the respective tubes to be closed. Control lines 21 and 22 control opening and closing of the valves 19 and 20.

The tube 14 is supplied from a first air-ram driven syringe 23 and the tube 15 is fed from a second air-ram driven syringe 24 and the apparatus enables polymer solution from either syringe 23 or syringe 24 to be ejected from the needles 10 towards the mandrel 11. A purge line 25 including a closure valve allows purging of the manifold 13.

The apparatus of FIG. 1 allows formation of an integral, uninterrupted fibrous structure of continuous polymeric filaments around the surface of the mandrel 11, the portions of the continuous filaments at the inside surface having a different polymeric composition from the portions of the same continuous filaments of the outside surface of the fibrous structure. This can be advantageous when the tubular fibrous structures are used for, for example, synthetic vascular grafts. It has been found that different polymers have different haemocompatibilities and that different polymers have different strength characteristics. In a particular example, one polyurethane has advantageous haemocompatibility but poor elastic properties, exhibiting high creep. A second polyurethane having a higher Young's modulus has satisfactory strength properties but poor haemocompatibility. The apparatus of FIG. 1, as will be described in the following example, allows production of a synthetic vascular graft having a thin inner lining of the first polyurethane on a wall of the second polyurethane, the graft, however, being formed of fibers spun continuously, with individual fibers changing composition between their ends to provide an integral, uninterrupted, fibrous structure.

EXAMPLE

The sequence of operation of the apparatus of FIG. 1 in this example is as follows:

1. Fill the syringe 24 with a first polymer dope and fill the syringe 23 with a second polymer dope.

2. Using the valves 19, 20 and 26, prime the tube 14 with the second polymer dope and then prime the tube 15 and the manifold 13 with first polymer dope.

3. With the valves 19 and 26 closed, commence electrostatic spinning with the first polymer dope contained in the syringe 24, the tube 15 and the manifold 13.

4. After a time, open the valve 19 and close the valve 20. After expression of remaining first polymer dope out of the needles 10, spinning continues in an uninterrupted fashion with second polymer.

Figure 2:
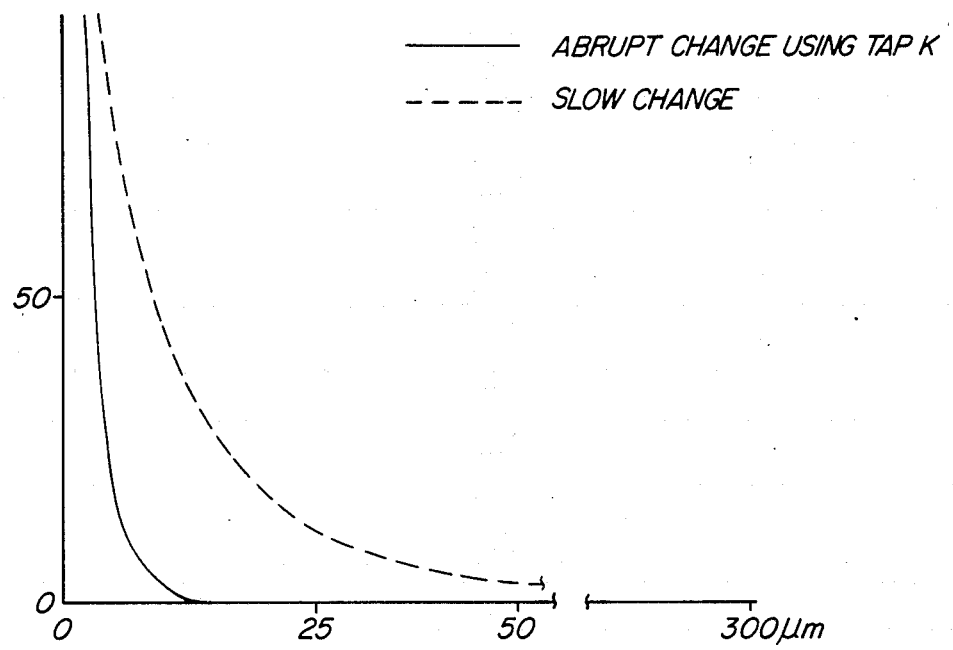
FIG. 2 is a graph illustrating concentration of one polymeric composition in a structure wall.

5. The abruptness of the transition from the first polymer dope to the second polymer dope is a function of the rate of flow of second polymer dope into the manifold 13 and the volume of the manifold 13, needles 10 and T junction 16. This transition can be controlled by the use of the valve 26 on the purge line 25 which can be used to vent at a variable rate remaining first polymer dope. The concentration gradient of the two polymers in the graft wall will follow a defined, controllable relationship as illustrated in FIG. 2 where the solid line shows an abrupt change where the valve 26 is used and the chain line shows a slow change.

If an abrupt change of polymer composition is desired in the filaments, the hold up volume in the various lines and the manifold 13 should be kept as small as possible, the manifold should be purged using valve 26 and the closing of valve 20 and opening of valve 19 should occur simultaneously and rather abruptly. If it is desired the polymer composition of the continuous filaments have a gradual change the reverse procedures should be used; i.e., a large hold up volume with a gradual opening and closing of the appropriate valves. In fact if desired valves 19 and 20 may both be left open for a period of time in order to obtain a mixture of polymer compositions in portions of the continuous filament.

Figure 3:
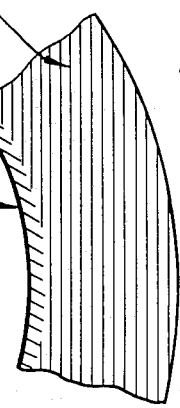
FIG. 3 is a part sectional view of a tubular fibrous structure produced by the apparatus of FIG. 1.

A further development of the first example arises in that on porosity testing, it was found that the permeability of the bi-layer graft was too high. A situation was envisaged where transmural flow of blood or plasma might lead to excessive blood platelet capture of the inner surface and compromise the thromboresistance of the graft. The solution here would be to include an outer layer of a third polymer, for example, one having a high Young's modulus, which when deposited on the second polymer produces a dense matrix with low interstitial volume. In this way, the overall graft wall permeability is determined by this outer layer. FIG. 3 shows in cross section part of a bi-layer graft. The further development would mean addition of an outer layer of a third polymer to the graft shown in FIG. 3.

Many different polymers can be used in the electrostatic spinning process. Several examples are given in U.S. Pat. No. 4,044,404, such as polyurethanes, polyamides and polyacrylonitrile, all of which can be spun from solution, and polytetrafluorethylene and polyesters which may be spun from dispersion. Water soluble polymers such as polyvinyl alcohol, polyvinyl pyrrolidone and polyethylene oxide may be spun from aqueous solution. Of course whichever polymers are to be used must be soluble in the same solvent if solution spinning is being used or they must melt at relatively close temperatures if melt spinning is being used.

The constraint on the fibrous structure and method of production according to the invention is that the two or more polymers used to vary the composition of the filaments during the spinning process must be either dispersible or alternatively soluble in the same solvent system. Thus it would be possible to spin with different polyurethanes, as used in the preferred example, or with different polyesters in dispersion, but it would not be possible to change, for example, from a polyurethane to a polyester unless a common solvent is used or the polymers have substantially the same melting temperatures.

It will also be appreciated that the properties of a particular polymeric composition may be varied by the presence of an additive, even if the polymeric composition itself does not vary along the length of a filament. For example, a silicone lubricant could be added to a polyurethane polymer and spun as the inner surface of a graft, the outer surface of the graft being the same polyurethane without the silicone lubricant. Such an example is included in the scope of the invention.

The advantage of the embodiments of grafts hereinbefore described are that the different layers can be optimized for particular properties, either in its morphology (e.g., porosity, pore shape, fiber size) or in its chemistry (e.g., type of polymer, presence of drug. For example, a drug such as heparin or prostacylin may be included in the inner layer to improve the property with regard to contacting blood). If such layers are built up discontinuously, lines of weakness exist between the contiguous surfaces and delamination is likely to occur at quite low mechanical stresses. The advantage of the method hereinbefore described is that it builds different layers into an integrally formed fibrous structure so that the successive wall components are merged in a well controlled way.

An illustration of the advantage of a bi-layer graft according to the example described is that in an initial canine common carotid trial, a 300% improvement in patency over non-laminated, single component grafts was found. Other possibilities, for example pledgets and drug releasing vascular grafts are also quite possible.

It will be appreciated that while the embodiments described relate to tubular fibrous structures for use as vascular grafts, the invention is equally applicable to planar fibrous structures such as mats and that such alternative structures would have wide applications.

I claim:

1. An integral fibrous structure comprising a plurality of a polymeric filaments, at least some of said filaments being continuous and extending from one side of the structure to the opposite side of the structure, the portions of said continuous filaments on one side of the structure being of a first polymeric composition and the portions of said continuous filaments on the opposite side of the structure being of a second polymer composition different from the first polymeric composition.

2. A fibrous structure according to claim 1 wherein the continuous filaments have a transition portion between the portion of said filaments on one side of the structure and the portions of the filaments on the opposite side of the structure, said transition portion comprising a mixture of said first and second polymeric compositions.

3. A fibrous structure according to claim 1 wherein the polymeric composition of the continuous filaments varies progressively between the two sides of the structure.

4. A fibrous structure according to claim 1 wherein the polymeric composition of the continuous filaments changes abruptly between the two sides of the structure to provide distinct layers within the fibrous structure having different polymeric composition.

5. A fibrous structure according to claim 1 or 2 in the form of a mat.

6. A fibrous structure according to claim 1 or 2 in the form of a tubular member.

7. A fibrous structure as claimed in claim 6 wherein the portions of the continuous filaments at the inner surface of the tubular member are of the first polymeric composition to provide compatability with material with which the inner surface will come into contact, and the portions of the continuous filaments at the outer surface of the tubular member are of the second polymeric composition to provide desirable strength characteristics and other physical properties to the tubular member.

* * * * *